(12) United States Patent
Arima (10) Patent No.: US 10,548,554 B2
(45) Date of Patent: Feb. 4, 2020

(54) RADIATION IMAGING APPARATUS, RADIATION IMAGING SYSTEM, RADIATION IMAGING METHOD, AND COMPUTER-READABLE MEDIUM

(71) Applicant: CANON KABUSHIKI KAISHA, Tokyo (JP)

(72) Inventor: Keisuke Arima, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 170 days.

(21) Appl. No.: 15/805,441

(22) Filed: Nov. 7, 2017

(65) Prior Publication Data

US 2018/0125441 A1 May 10, 2018

(30) Foreign Application Priority Data

Nov. 9, 2016 (JP) ................................ 2016-219179

(51) Int. Cl.
*G16H 30/20* (2018.01)
*A61B 6/00* (2006.01)
*A61B 6/10* (2006.01)
*G16H 30/40* (2018.01)

(52) U.S. Cl.
CPC ............ *A61B 6/5205* (2013.01); *A61B 6/107* (2013.01); *A61B 6/461* (2013.01); *A61B 6/54* (2013.01); *A61B 6/563* (2013.01); *G16H 30/20* (2018.01); *A61B 6/4283* (2013.01); *G16H 30/40* (2018.01)

(58) Field of Classification Search
CPC ......... A61B 6/54; A61B 6/563; A61B 6/4405; A61B 6/461; A61B 6/5205; A61B 6/42; A61B 6/465; G16H 30/20; G16H 30/40
See application file for complete search history.

(56) References Cited

U.S. PATENT DOCUMENTS

| 2011/0051896 A1* | 3/2011 | Abe ........................ A61B 6/00 378/98.8 |
| 2013/0230141 A1* | 9/2013 | Miyachi ................... H05G 1/30 378/62 |

FOREIGN PATENT DOCUMENTS

JP           2009-053661 A     3/2009

* cited by examiner

*Primary Examiner* — David P Porta
*Assistant Examiner* — Fani Boosalis
(74) *Attorney, Agent, or Firm* — Carter, DeLuca & Farrell LLP (57) ABSTRACT

Provided is a radiation imaging apparatus, including: an information acquisition unit configured to acquire information on a radiation image from a detection apparatus configured to take the radiation image by detecting radiation; a transfer request unit configured to transmit to the detection apparatus, based on the information, a transfer request signal for requesting transfer of a radiation image untransferred and stored in the detection apparatus; and an image acquisition unit configured to acquire the radiation image from the detection apparatus.

17 Claims, 7 Drawing Sheets

RADIATION IMAGING APPARATUS, RADIATION IMAGING SYSTEM, RADIATION IMAGING METHOD, AND COMPUTER-READABLE MEDIUM

BACKGROUND OF THE INVENTION

Field of the Invention

The present invention relates to a radiation imaging apparatus, a radiation imaging system, a radiation imaging method, and a computer-readable medium.

Description of the Related Art

There has been known a radiation imaging apparatus that uses a radiation detection cassette configured to detect an intensity distribution of radiation (e.g., X ray) that has passed through a subject to take a radiation image of the subject. Such a radiation imaging apparatus is used mainly in, for example, a medical field or an industrial field. In recent years, there has also been widely adopted a technology of converting radiation that has passed through a subject (object) into an electric signal to acquire a radiation image as digital data.

In Japanese Patent Application Laid-Open No. 2009-53661, there is proposed a method involving performing communication between a radiation detection cassette and a host computer.

In recent years, there has been developed a radiation detection cassette including a large-capacity memory and capable of storing radiation images in the large-capacity memory. In this case, the radiation imaging apparatus collectively acquires the radiation images stored in the radiation detection cassette.

However, when the radiation images stored in the large-capacity memory of the radiation detection cassette are acquired, there has been a problem in that the acquisition of the radiation image cannot be controlled finely on the radiation imaging apparatus side.

SUMMARY OF THE INVENTION

The present invention has been made in view of the above-mentioned problem, and provides a radiation imaging apparatus, a radiation imaging system, a radiation imaging method, and a computer-readable medium, which are capable of controlling finely acquisition of a radiation image from a radiation detection cassette.

According to one aspect of the invention, provided is a radiation imaging apparatus, including: an information acquisition unit configured to acquire information on a radiation image from a detection apparatus configured to take the radiation image by detecting radiation; a transfer request unit configured to transmit to the detection apparatus, based on the information, a transfer request signal for requesting transfer of an untransferred radiation image stored in the detection apparatus; and an image acquisition unit configured to acquire the radiation image from the detection apparatus.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

(First Embodiment)

Figure 1:
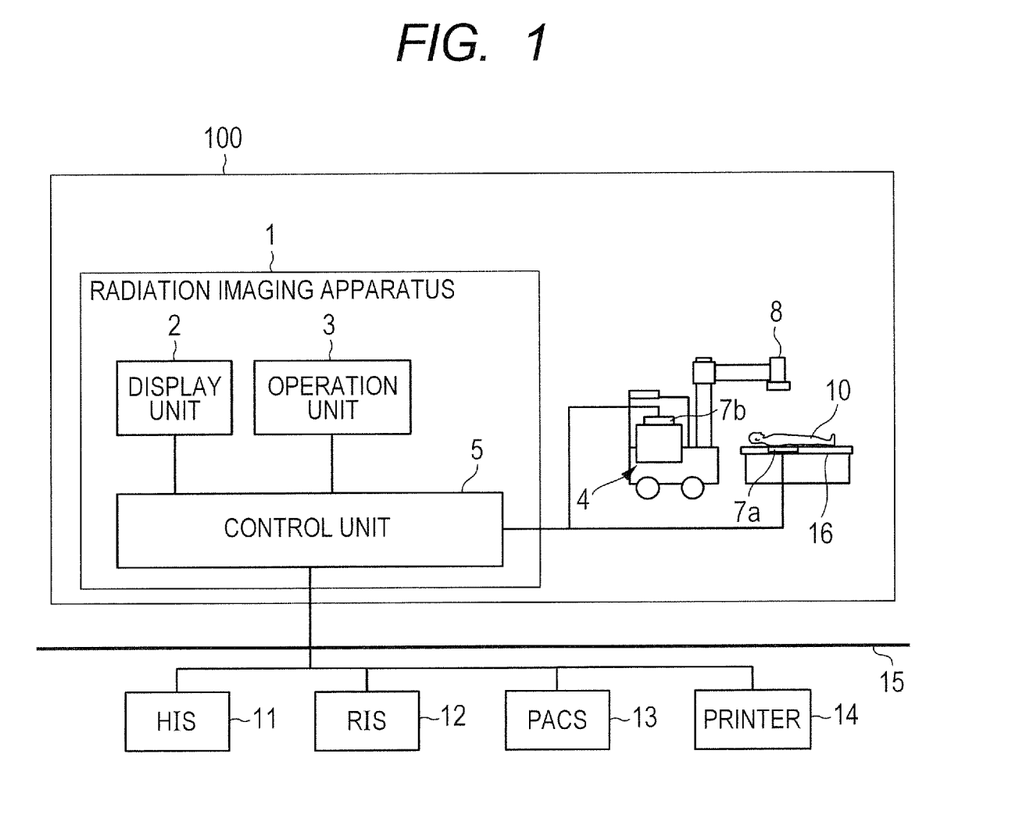
FIG. 1 is a diagram for illustrating a configuration example of a radiation imaging system according to a first embodiment of the present invention.

A first embodiment of the present invention is described with reference to FIG. 1. FIG. 1 is a diagram for illustrating a configuration example of a radiation imaging system according to the first embodiment. As illustrated in FIG. 1, the radiation imaging system according to the first embodiment includes a radiation imaging apparatus 1 and a hospital information system (HIS) 11 configured to manage the progress of an examination.

The radiation imaging system according to the first embodiment also includes a radiology information system (RIS) 12 configured to transmit an examination order to the radiation imaging apparatus 1. Further, to the radiation imaging system according to the first embodiment, a picture archiving and communication system (PACS) 13 configured to manage a radiation image and a printer 14 configured to print a radiation image for output are connected.

The HIS 11 is a hospital management system, and includes a server configured to manage billing information. To perform radiation imaging, an operator inputs an examination instruction through a terminal (input unit) of the HIS 11. Then, the HIS 11 transmits request information to a radiation department of a hospital requested to perform the radiation imaging. The request information is referred to as "examination order". The examination order includes the name of a department name that has requested radiation imaging, an examination ID, an examination item, and patient information (subject-to-be-examined information) on a person to be examined (subject to be examined).

When the RIS 12 receives the examination order, the radiation department adds imaging information on the radiation imaging (e.g., identification information of an examination item (examination ID), imaged body part information, imaging direction information, and procedure information) to the examination order, and transmits the resultant examination order to the radiation imaging apparatus 1. The radiation imaging apparatus 1 performs radiation imaging in accordance with the received examination order. The radiation imaging apparatus 1 acquires a taken radiation image, generates examination information in which the radiation image and the examination order are associated with each other, and outputs the examination information together with the radiation image.

The PACS 13 is a server configured mainly to manage an image. With a high-definition monitor connected to the PACS 13, inspection of the radiation image, detailed post-processing, and diagnosis work are performed. In order to subject the radiation image to such processing, the radiation image taken by the radiation imaging apparatus 1 is transmitted to the PACS 13.

Further, execution information on the examination performed in the radiation imaging apparatus 1 (e.g., image ID, and date and time of imaging) is transmitted to the HIS 11. The execution information transmitted to the HIS 11 is used for billing processing to be performed after the examination as well as for the management of the progress of the examination.

The radiation imaging apparatus 1, the HIS 11, the RIS 12, the PACS 13, and the printer 14 are connected to one another via a network 15 constructed by, for example, a local area network (LAN) or a wide area network (WAN).

Each of those apparatus includes one or more computers. The computer includes, for example, a CPU or other such main control unit, and a read only memory (ROM), a random access memory (RAM), or other such storage unit. The computer may also include a network card or other such communication unit, and a keyboard, a display, a touch panel, or other such input/output unit. Those units of the computer are electrically connected to one another via a bus, for example, and are controlled by the main control unit executing programs stored in the storage unit.

As illustrated in FIG. 1, in an imaging room 100, the radiation imaging apparatus 1 configured to perform radiation imaging is installed. Further, in the imaging room 100, a radiation generation apparatus 4 configured to generate radiation, detection apparatus 7a and 7b configured to take a radiation image by detecting the radiation that has passed through the person to be examined 10, and an imaging table 16 are installed.

The radiation imaging apparatus 1 includes a display unit 2 configured to display a radiation image and various kinds of information, an operation unit 3 to be operated by the operator, and a control unit 5 configured to control the components of the radiation imaging apparatus 1.

The radiation generation apparatus 4 is configured to set conditions of radiation imaging to be performed in the radiation generation unit 8 to control the radiation generation unit 8. The radiation generation unit functions as a radiation source configured to generate radiation. The radiation generation unit 8 is implemented by, for example, a radiation tube, and is configured to apply radiation to the person to be examined 10 (e.g., specific body part of person to be examined).

The radiation generation unit 8 is capable of applying radiation in a desired radiation application range. On a radiation surface of the radiation generation unit 8, a diaphragm (not shown) for shielding radiation is installed. The operator can adjust the radiation range of radiation applied from the radiation generation unit 8 by controlling the diaphragm for shielding the radiation.

The radiation imaging system includes the detection apparatus 7a and 7b configured to detect radiation applied from the radiation generation unit 8. The detection apparatus 7a and 7b are configured to detect radiation that has passed through the person to be examined to output image data corresponding to the radiation. The image data can be rephrased as "radiation image". The detection apparatus 7a and 7b are hereinafter collectively referred to simply as "detection apparatus 7".

Specifically, the detection apparatus 7 detects the radiation that has passed through the person to be examined 10 as electric charges corresponding to a transmitted radiation dose. For example, the detection apparatus 7 uses a direct conversion sensor that uses, for example, a-Se, which converts radiation into electric charges, to directly convert radiation into electric charges, or an indirect sensor that uses a scintillator, for example, CsI and a photoelectric conversion element, for example, a-Si.

The detection apparatus 7 is a cassette-type detection apparatus that is portable, and is carried to the imaging room 100 in which the examination is performed along with the radiation generation apparatus 4. The detection apparatus 7a and 7b having different sizes are used appropriately depending on the size of an object and an imaged body part to perform radiation imaging.

The detection apparatus 7 performs A/D conversion of the detected electric charges to generate image data, and stores the image data in a storage (not shown). The detection apparatus 7 is capable of adding information (image ID, date and time of imaging, and transfer state of image data) to the image data, and transferring the information to the radiation imaging apparatus 1 along with the image data.

The display unit 2 is implemented by, for example, a liquid crystal display, and is configured to display various types of information to the operator (e.g., imaging engineer or doctor). The operation unit 3 includes an input unit 28 and a designation unit 29, and is used to operate processing performed in the radiation imaging apparatus 1. The operation unit 3 is constructed by, for example, a mouse and an operation button, and is configured to input various types of instructions from the operator to respective components of the radiation imaging apparatus 1. The display unit 2 and the operation unit 3 may be implemented as a touch panel in which those units are integrally formed.

The control unit 5 of the radiation imaging apparatus 1 is connected to the detection apparatus 7 via a wireless LAN. The image data, a control signal, and the like are transmitted and received between the control unit 5 and the detection apparatus 7. In other words, the image data stored in the detection apparatus 7 by the radiation imaging is output (transferred) to the control unit 5 via the wireless LAN.

Figure 2:
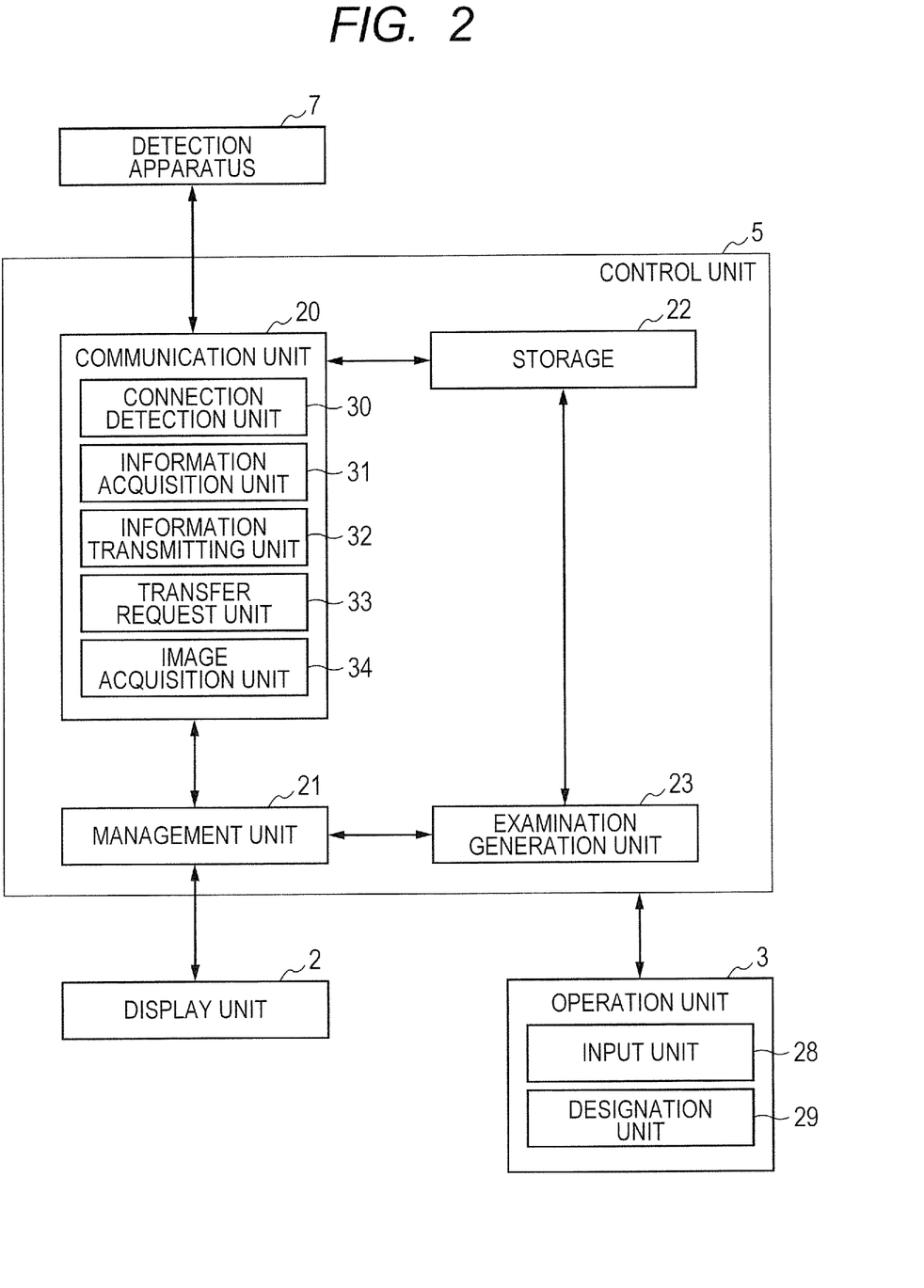
FIG. 2 is a diagram for illustrating a configuration example of a radiation imaging apparatus according to the first embodiment.

The radiation imaging system according to the present invention is described in detail with reference to FIG. 2. The radiation imaging apparatus 1 includes the control unit 5 configured to perform image processing of the radiation image output from the detection apparatus 7 to generate an image. The control unit 5 has a function of applications to be operated on a computer. The control unit 5 is configured to control the operation of the detection apparatus 7 and to output a radiation image and a graphical user interface (GUI) to the display unit 2.

The control unit 5 includes a communication unit configured to communicate to/from the detection apparatus 7, a management unit 21 configured to manage the state of the detection apparatus 7, and a storage 22 configured to store the radiation image output from the detection apparatus 7 and various types of information including the examination order output from an external apparatus, for example, the RIS. The control unit 5 also includes an examination generation unit 23 configured to generate the examination information in which the radiation image and the examination order are associated with each other.

The communication unit 20 includes a connection detection unit 30, an information acquisition unit 31, an information transmitting unit 32, a transfer request unit 33, and an image acquisition unit 34.

The connection detection unit 30 is configured to detect a communication connection and disconnection between the radiation imaging apparatus 1 and the detection apparatus 7. The information acquisition unit 31 is configured to receive the information stored in the detection apparatus 7 (information on the radiation image). The information acquisition unit 31 is configured to acquire the information on a radiation image from the detection apparatus 7 configured to take the radiation image by detecting radiation.

The information transmitting unit 32 is capable of transmitting to the detection apparatus 7 imaging information on the radiation imaging, such as patient information (subject-to-be-examined information), identification information of an examination, imaged body part information, imaging direction information, and procedure information. When receiving the imaging information, the detection apparatus 7 stores the imaging information along with the image data acquired in accordance with the imaging information. Further, the detection apparatus 7 stores the information on the radiation image taken by the radiation imaging along with the image data.

The transfer request unit 33 is configured to transmit to the detection apparatus 7 a transfer request signal for requesting transfer of untransferred pieces of image data stored in the detection apparatus 7. The image acquisition unit 34 is configured to receive the image data from the detection apparatus 7.

The management unit 21 is configured to manage the information acquired by the communication unit 20 along with detection apparatus information on the detection apparatus 7 (e.g., name of the detection apparatus 7 and signal strength thereof). Those pieces of information are displayed on the display unit 2.

The examination generation unit 23 is configured to generate the examination information in which the radiation image and the examination order are associated with each other. The examination generation unit 23 is configured to acquire from the detection apparatus 7 at least one of the patient information (subject-to-be-examined information) on the subject to be examined of the radiation imaging, the imaging information on the radiation imaging, the detection apparatus information on the detection apparatus, or the information on the radiation image, as supplementary information attached to the radiation image. The examination generation unit 23 is configured to generate the examination information in which the radiation image and the examination order relating to an examination request for the radiation imaging are associated with each other based on, of the supplementary information, related information related to the examination order.

When the related information related to the examination order (e.g., patient information or imaging information) is attached to the radiation image received from the detection apparatus 7, the examination generation unit 23 generates the examination information using the related information. When the related information related to the examination order is not attached to the radiation image received from the detection apparatus 7, the operation unit 3 inputs the related information for associating the radiation image and the examination order with each other, and the examination generation unit 23 generates the examination information using the related information.

In this case, the input unit 28 inputs, based on the supplementary information, the related information for associating the radiation image and the examination order with each other, and the examination generation unit 23 generates the examination information based on the input related information. For example, when the input unit 28 inputs an image ID corresponding to the examination order based on the supplementary information, the radiation image and the examination order are associated with each other to generate the examination information.

The storage 22 is configured to store the radiation image output from the detection apparatus 7 and the examination information generated by the examination generation unit 23.

Figure 3:
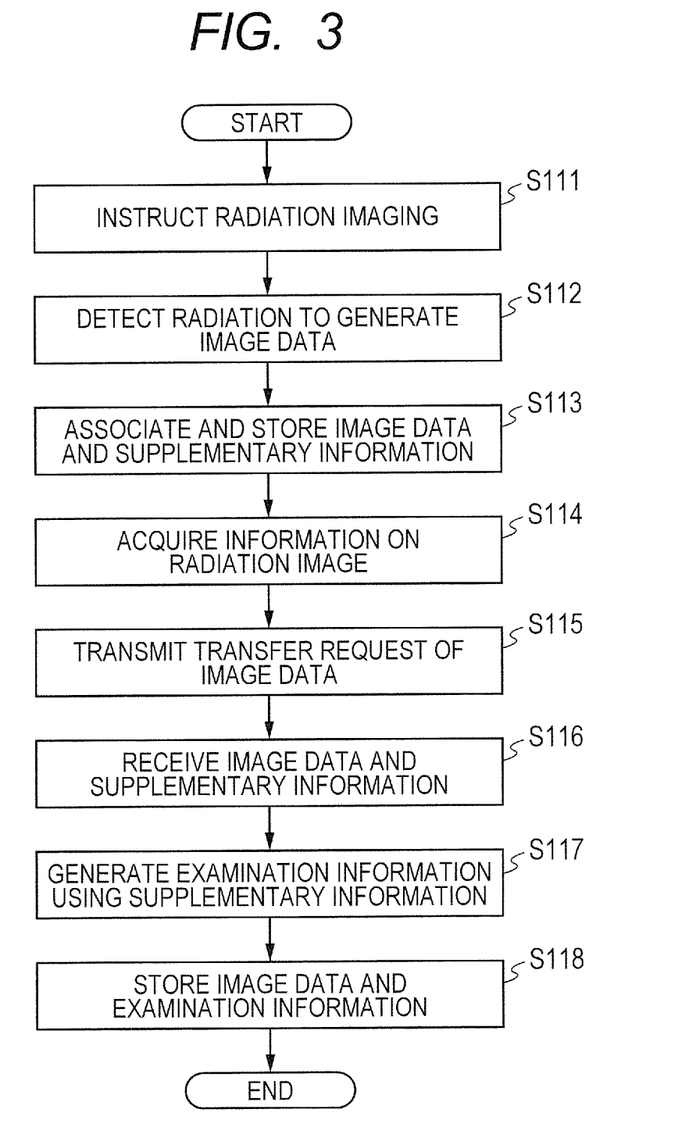
FIG. 3 is a flowchart for illustrating an operation of the radiation imaging system according to the first embodiment.
Figure 4:
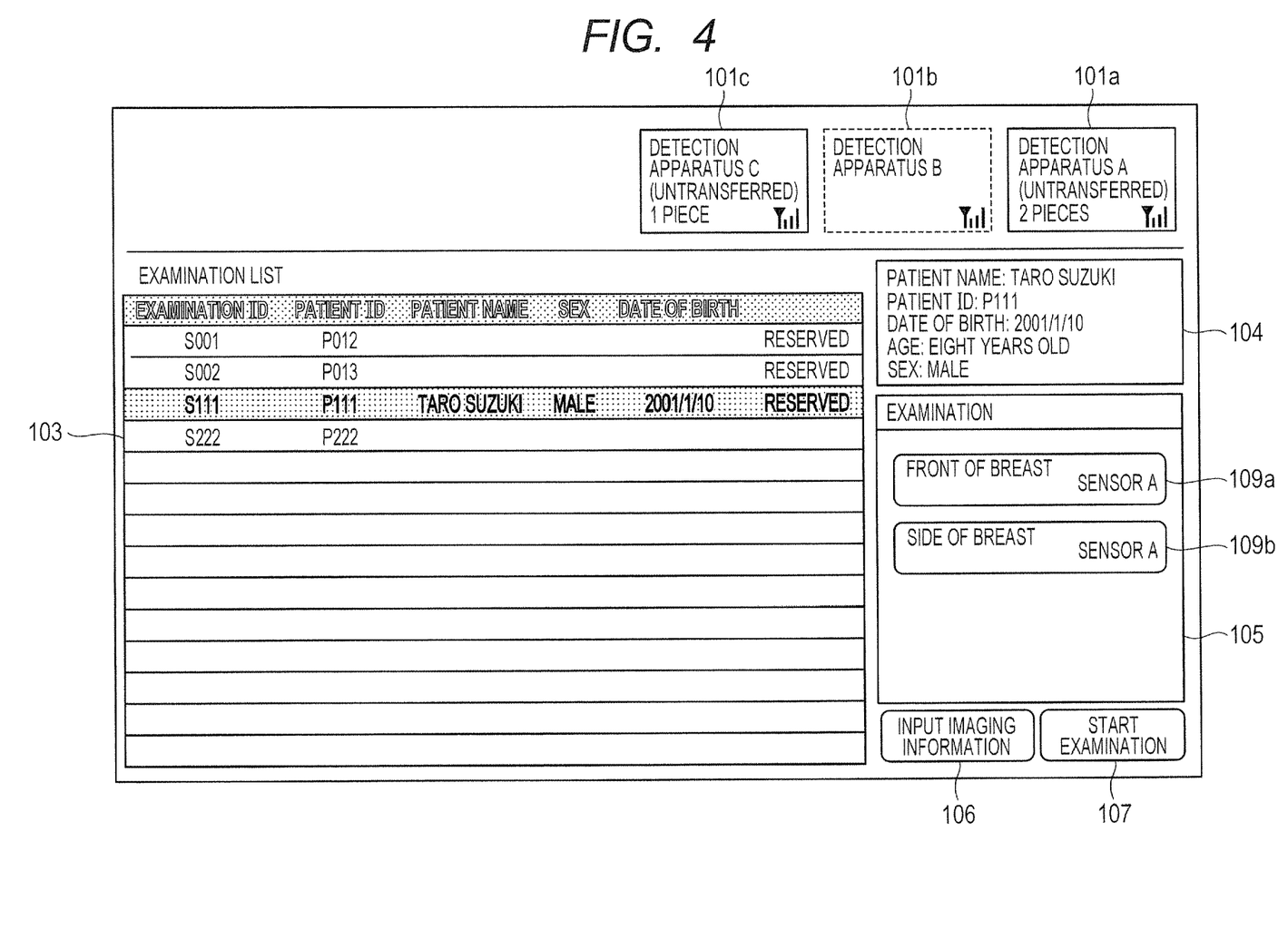
FIG. 4 is a diagram for illustrating a display mode of the radiation imaging system according to the first embodiment.

FIG. 3 is a flowchart for illustrating an operation of the radiation imaging system according to the first embodiment. FIG. 4 is an illustration of a display mode of the display unit 2 of the radiation imaging system according to the first embodiment. The display unit 2 includes detection apparatus display sections 101a, 101b, and 101c, an examination list 103, a patient information display section 104, an imaging information display section 105, an imaging information input section 106, and a start instruction section 107. The detection apparatus display sections 101a, 101b, and 101c are hereinafter collectively referred to simply as "detection apparatus display section 101".

The detection apparatus display section 101 displays the detection apparatus information and other information on the connected detection apparatus 7. The examination list 103 displays the examination order including an examination ID in a list format. The patient information display section 104 displays the patient information of the examination order designated in the examination list 103. The imaging information display section 105 displays the imaging information added to the examination order designated in the examination list 103. The imaging information input section 106 is used to input the imaging information. The start instruction section 107 is used to give an instruction to start the radiation imaging in accordance with the imaging information (Step S111).

The radiation generation apparatus 4 applies radiation to the detection apparatus 7, and the detection apparatus 7 detects the radiation to generate image data (Step S112). In this case, the detection apparatus 7 generates image data under a state in which the communication connection to the radiation imaging apparatus is not established, and associates the detection apparatus information and the information with the image data as the supplementary information and stores the resultant image data in the storage (Step S113).

The connection detection unit 30 is configured to detect a communication connection between the radiation imaging apparatus 1 and the detection apparatus 7. When the connection detection unit 30 detects the communication connection to the detection apparatus 7, the information acquisition unit 31 acquires information on the radiation image (Step S114). In response to the connection detection, the management unit 21 acquires via the information acquisition unit 31 the information stored in the detection apparatus 7. The information on the radiation image includes information such as the image ID, the date and time of imaging, and a transfer state of the image data (e.g., completion/incompletion of transfer, number of transferred images, number of untransferred images, and date and time of transfer).

The information acquisition unit 31 acquires, as the information on the radiation image, information on at least one of the image ID, date of imaging, time of imaging, completion of transfer, incompletion of transfer, number of transferred images, number of untransferred images, date of transfer, and time of transfer of the radiation image. The information acquisition unit 31 acquires the number of untransferred radiation images (pieces of image data) as the information, and displays the information on the display unit 2. The management unit 21 calculates the number of untransferred images based on the information acquired by the information acquisition unit 31.

The display unit 2 (detection apparatus display section 101) displays the number of untransferred radiation images along with the detection apparatus information such as the name of the detection apparatus 7 and the signal strength thereof. In this manner, the display unit 2 (detection apparatus display section 101) displays the information on the radiation image. In FIG. 4, the fact that a detection apparatus A has not transferred two pieces of image data yet and a detection apparatus C has not transferred one piece of image data yet is illustrated.

When a plurality of detection apparatus are connected to the radiation imaging apparatus 1, the detection apparatus display sections 101 are arranged in the order in which the connections to the detection apparatus are detected. FIG. 4 is an illustration of an example in which the connections to the radiation imaging apparatus 1 are detected in the order of the detection apparatus A, a detection apparatus B, and the detection apparatus C, and the detection apparatus display sections 101*a*, 101*b*, and 101*c* are displayed to be arranged in order from the right side of the detection apparatus display sections 101. In this manner, the display unit 2 displays pieces of the information preferentially in the order in which the connection detection unit 30 detects a communication connection to the detection apparatus 7.

Further, the detection apparatus display sections 101*a* and 101*c* for displaying the detection apparatus information and other information on the detection apparatus A and C holding untransferred images function as an operation unit for giving an instruction to transfer an untransferred piece of image data. For example, the detection apparatus display sections 101*a* and 101*c* are displayed as buttons, and when one of the buttons is touched, a screen for transmitting an instruction to transfer the image data to a corresponding one of the detection apparatus A and C is displayed.

In this manner, the display unit 2 displays the information on an untransferred radiation image in a display mode different from that of the information on a transferred radiation image, and the transfer request unit transmits a transfer request signal to the detection apparatus 7 when the display mode of the information on the untransferred radiation image is operated.

Meanwhile, the detection apparatus display section 101*b* for displaying the detection apparatus information and other information on the detection apparatus B, which does not hold an untransferred radiation image, is displayed in a mode that does not allow a transfer instruction operation. For example, even when the detection apparatus display section 101*b* is touched, an instruction to transfer the image data is not executed.

Further, the detection apparatus A and C, which hold untransferred radiation images, the detection apparatus B, which does not hold an untransferred radiation image, may be distinguished from each other such that the detection apparatus A and C holding the untransferred radiation images are preferentially displayed. For example, the detection apparatus display sections 101*a* and 101*c* for displaying the information on the detection apparatus A and C and the like may be displayed with priority over the detection apparatus display section 101*b* for displaying the information on the detection apparatus B and the like such that the detection apparatus display sections 101 are displayed in the order of the detection apparatus display sections 101*a*, 101*c*, and 101*b*. In this manner, the display unit 2 may display the information on an untransferred radiation image with priority over the information on a transferred radiation image.

Figure 5A:
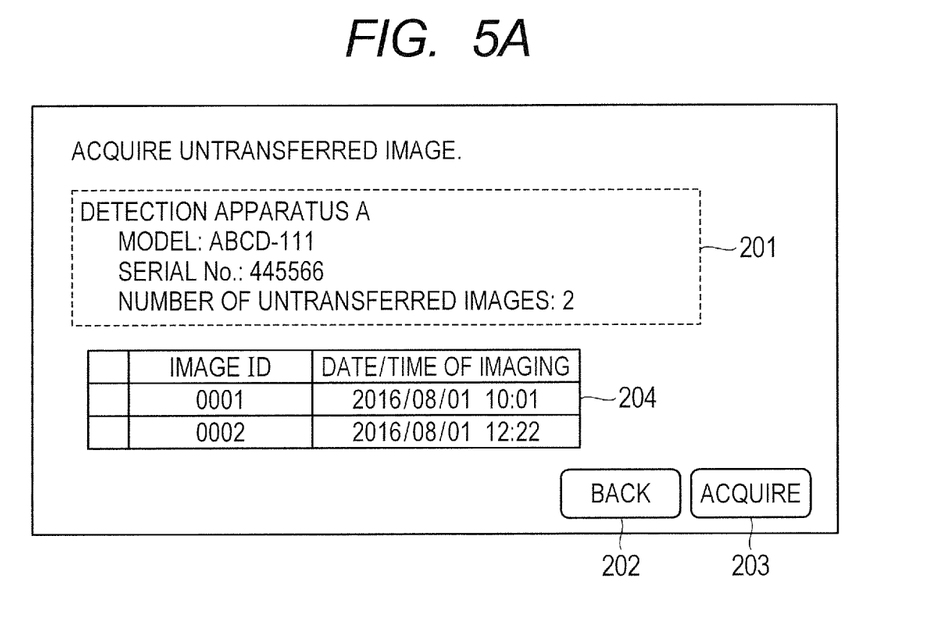
FIG. 5A is a diagram for illustrating an example of a display screen displayed when transfer of an untransferred radiation image is requested in the first embodiment.

FIG. 5A is a diagram for illustrating a screen of the display unit 2 displayed when a transfer instruction is given from the detection apparatus display section 101*a*. In a detection apparatus information display section 201, the detection apparatus information on the detection apparatus A instructed to transfer the radiation image is displayed. The detection apparatus information includes the name, model name, serial number, and the like of the detection apparatus. Further, in the detection apparatus information display section 201, the number of untransferred pieces of image data held by the detection apparatus A is displayed.

In an information display section 204, the information received from the detection apparatus 7 is displayed in a list format. For example, the image ID, date and time of imaging, and other such items of the radiation image acquired by the detection apparatus 7 are displayed in the information display section 204.

When an "acquire" button 203 is pressed, the communication unit 20 transmits a transfer request of the image data to the detection apparatus 7 (Step S115). The transfer request unit 33 transmits to the detection apparatus 7, based on the information, the transfer request signal for requesting transfer of the untransferred radiation image stored in the detection apparatus 7. In response to the transfer request, the detection apparatus 7 outputs the stored image data along with the supplementary information attached to the image data (e.g., detection apparatus information and information), and transmits the image data and the supplementary information to the communication unit 20. In response to the transfer request, the detection apparatus 7 may collectively output the untransferred image data and the supplementary information, and transmit the image data and the supplementary information to the communication unit 20.

The radiation imaging apparatus 1 receives the untransferred image data and the supplementary information from the detection apparatus 7 (Step S116). The image acquisition unit 34 acquires the image data (radiation image), and the information acquisition unit 31 acquires the supplementary information. While the radiation imaging apparatus 1 is receiving the untransferred image data and the supplementary information, the information display section 204 displays a transfer state of the image data (e.g., completion of transfer, incompletion of transfer, the number of transferred pieces of image data, the number of untransferred pieces of image data, and date and time of transfer).

Figure 5B:
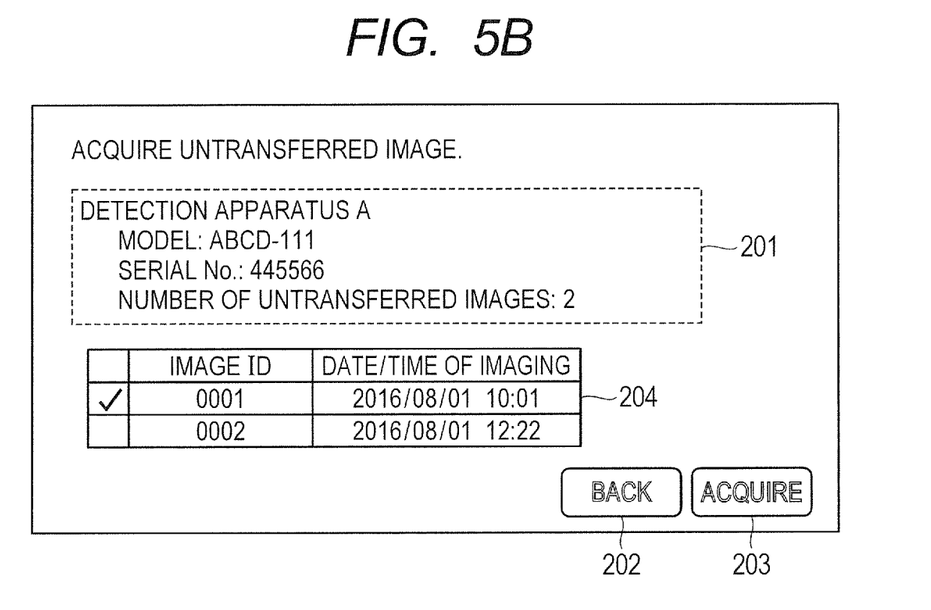
FIG. 5B is a diagram for illustrating an example of a display screen displayed during transfer of an untransferred radiation image.

In FIG. 5B, the completion of transfer and the incompletion of transfer are displayed. To image data that has been transferred, a checkmark indicating the completion of transfer is attached in the information display section 204. When a checkmark is not attached to image data, the information display section 204 indicates the incompletion of transfer of the image data.

When the reception of all pieces of image data is completed, the examination generation unit 23 generates the examination information using the received supplementary information (Step S117). The examination generation unit 23 acquires from the detection apparatus 7 at least one of the patient information (subject-to-be-examined information) on the subject to examined of the radiation imaging, the imaging information on the radiation imaging, the detection apparatus information on the detection apparatus, or the information on the radiation image, as supplementary information attached to the radiation image. The examination generation unit 23 generates the examination information in which the radiation image and the examination order relating to an examination request for the radiation imaging are associated with each other based on, of the supplementary information, related information related to the examination order.

For example, the detection apparatus information and other information on the detection apparatus 7 are attached to the image data, and hence those pieces of information may be used as the related information. Further, the detection apparatus information and other information on the detection apparatus 7 may be used as the execution information.

When the related information related to the examination order is not attached to the image data, the supplementary information corresponding to the related information is attached to the image data in accordance with a predetermined rule. For example, as the supplementary information corresponding to the related information (e.g., patient information), the detection apparatus 7 attaches a number to the image data in ascending order. Further, the detection apparatus 7 includes a sectioning button for sectioning the supplementary information. When the sectioning button is pressed, the number is attached to the image data as the supplementary information (e.g., patient information), and until the sectioning button is pressed next, the same number is attached to the image data as the supplementary information (patient information).

In this manner, based on the section of at least one of the subject-to-be-examined information, the imaging information, the detection apparatus information, or other information, the supplementary information may be attached to the radiation image for each section.

When the operation unit 3 inputs corresponding related information based on the supplementary information corresponding to the related information, the examination generation unit 23 generates the examination information using the related information. For example, the operation unit 3 inputs the corresponding patient information based on the number attached to the image data (number corresponding to patient information). As a result, the number and the patient information are associated with each other, and the examination generation unit 23 uses the number associated with the patient information to associate the radiation image and the examination order with each other, to thereby generate the examination information.

The storage 22 stores the radiation image output from the detection apparatus 7 and the examination information generated by the examination generation unit 23 (Step S118). Further, the radiation imaging has already been executed at the time when the examination information is generated, and hence to start an examination status, the start of the examination is notified to the HIS 11 and the RIS 12. For example, through display of "reserved" in an examination field of the examination list 103 of the display unit 2, the notification of the start of the examination is executed. A "back" button 202 is a button to be pressed to close the screen to return to the previous screen (screen of FIG. 4).

As described above, not on the detection apparatus side but on the radiation imaging apparatus side, display of the number of untransferred pieces of image data, execution of an instruction to transfer untransferred image data, display of a transfer state of untransferred image data, and association of the examination order with the image data can be performed, for example. As a result, the radiation imaging apparatus can control acquisition of a radiation image finely.

(Second Embodiment)

A radiation imaging system according to a second embodiment of the present invention is described. Descriptions of the same components, functions, and operations as those of the first embodiment described above are omitted, and differences from the first embodiment are mainly described. A configuration of the radiation imaging system according to the second embodiment is the same as that of the first embodiment, and hence a description thereof is omitted.

One of the differences from the first embodiment is that the detection apparatus 7 receives the related information from the radiation imaging apparatus 1 and attaches the related information to the image data. For example, before the radiation imaging, the detection apparatus 7 receives the related information (e.g., examination order, patient information, and imaging information) from the radiation imaging apparatus 1, and generates the examination information using the related information.

Figure 6:
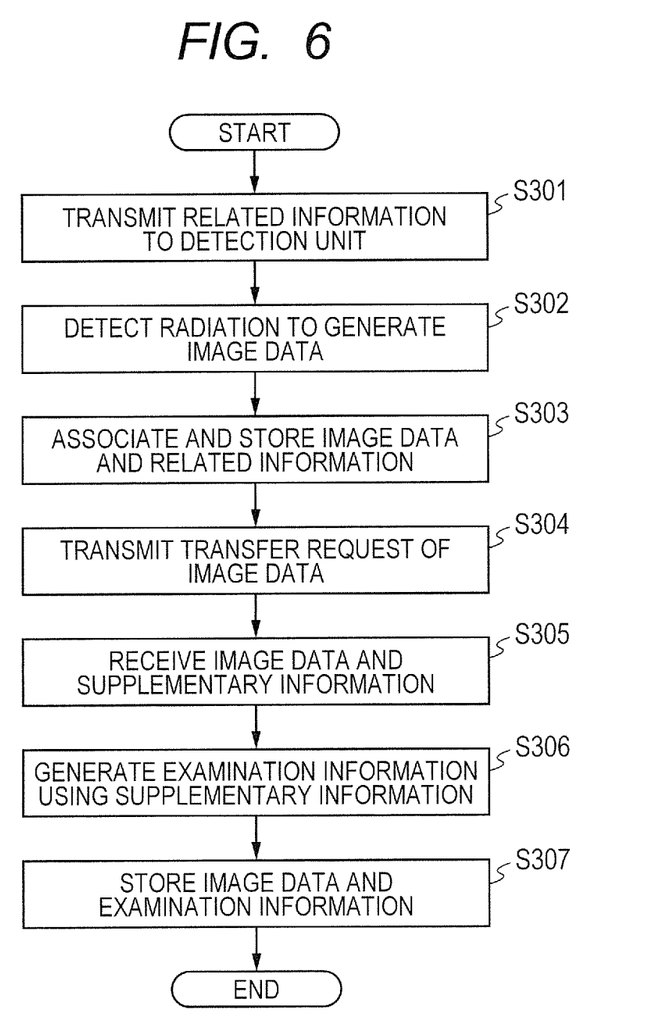
FIG. 6 is a flowchart for illustrating an operation of a radiation imaging system according to a second embodiment of the present invention.

FIG. 6 is a flowchart for illustrating an operation of the radiation imaging system according to the second embodiment. Before the radiation imaging, the control unit 5 outputs to the detection apparatus 7 at least one of the examination order, patient information, and imaging information of radiation imaging to be executed as the related information (Step S301). Specifically, the information transmitting unit 32 transmits to the detection apparatus 7 at least one of the examination order relating to an examination request for the radiation imaging, the patient information (subject-to-be-examined information) relating to the subject to be examined of the radiation imaging, and the imaging information relating to the radiation imaging, as the related information related to the examination order.

The examination order designated in the examination list 103, the patient information of the examination order designated in the examination list 103, and the imaging information displayed in the imaging information display section 105 are output as the related information from the communication unit 20 to the detection apparatus 7. The related information to be output may be, instead of the examination order, the patient information, and the imaging information themselves, identification information allowing those pieces of related information to be identified. In this case, the related information is identified by comparing, based on identification information of the related information, collation information held in the storage 22 with the identification information. The detection apparatus 7 temporarily stores the related information as the supplementary information attached to the image data.

The radiation generation apparatus 4 applies radiation to the detection apparatus 7, and the detection apparatus 7 detects the radiation to generate image data (Step S302).

The detection apparatus 7 associates the received related information and the image data with each other, and stores the resultant in the storage (not shown) provided in the detection apparatus 7. The detection apparatus 7 associates the information with the image data, and stores the resultant in the storage provided in the detection apparatus 7 (Step S303).

Figure 7:
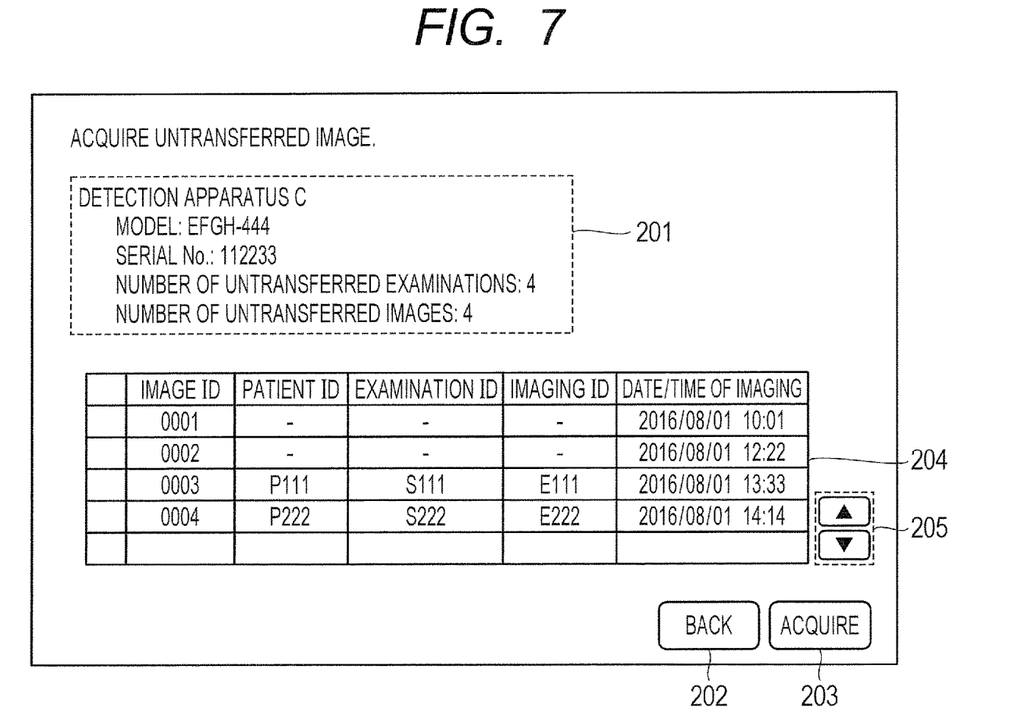
FIG. 7 is a diagram for illustrating an example of a display screen displayed when transfer of an untransferred radiation image is requested in the second embodiment.

The operator establishes a communication connection between the radiation imaging apparatus 1 and the detection apparatus 7, and transmits a transfer request of the image data from the display unit 2 to the detection apparatus 7. FIG. 7 is a diagram for illustrating an example of a transfer request screen to be displayed on the display unit 2. In the information display section 204, the information received from the detection apparatus 7 is displayed in a list format. For example, the image ID, date and time of imaging, and other such items of the radiation image acquired by the detection apparatus 7 are displayed. Further, items of the related information (e.g., examination order, patient information, and imaging information) received by the detection apparatus 7 are displayed.

In the detection apparatus information display section 201, the number of untransferred pieces of image data held by the detection apparatus C is displayed. Further, in the detection apparatus information display section 201, the number of examinations corresponding to the number of untransferred pieces of image data held by the detection apparatus C is displayed. The information acquisition unit 31 causes the display unit 2 (detection apparatus information display section 201) to display the number of examinations corresponding to the number of untransferred pieces of radiation image data as the supplementary information.

When an order change button 205 (designation unit 29) is operated, a display order of the information display section 204 is changed. When the "acquire" button 203 is pressed, the radiation imaging apparatus 1 transmits a transfer request to the detection apparatus 7 in the display order of the information display section 204 (Step S304).

In this manner, the order change button 205 (designation unit 29) is used to designate a transfer order of untransferred radiation images. Further, the designation unit 29 may designate a transfer order of untransferred radiation images by sorting pieces of information displayed in the information display section 204.

The control unit 5 receives the image data and the supplementary information that are output from the detection apparatus 7 in response to the transfer request (Step S305).

The examination generation unit 23 generates the examination information using the supplementary information (Step S306). In the second embodiment, at least one of the examination order, the patient information, or the imaging information is transmitted to the detection apparatus 7 as the related information, and hence an untransferred radiation image is transferred to the radiation imaging apparatus 1 with the related information being attached to the radiation image. The examination generation unit 23 generates the examination information in which the radiation image and the examination order are associated with each other based on the related information of the supplementary information attached to the radiation image.

The supplementary information includes various types of information (e.g., examination order, patient information, imaging information, detection apparatus information, and other information) or identification information allowing those pieces of related information to be identified. When receiving the identification information of the supplementary information, the radiation imaging apparatus 1 compares the identification information with the collation information held in the storage 22 to display various types of information, for example, a patient name.

Figure 8:
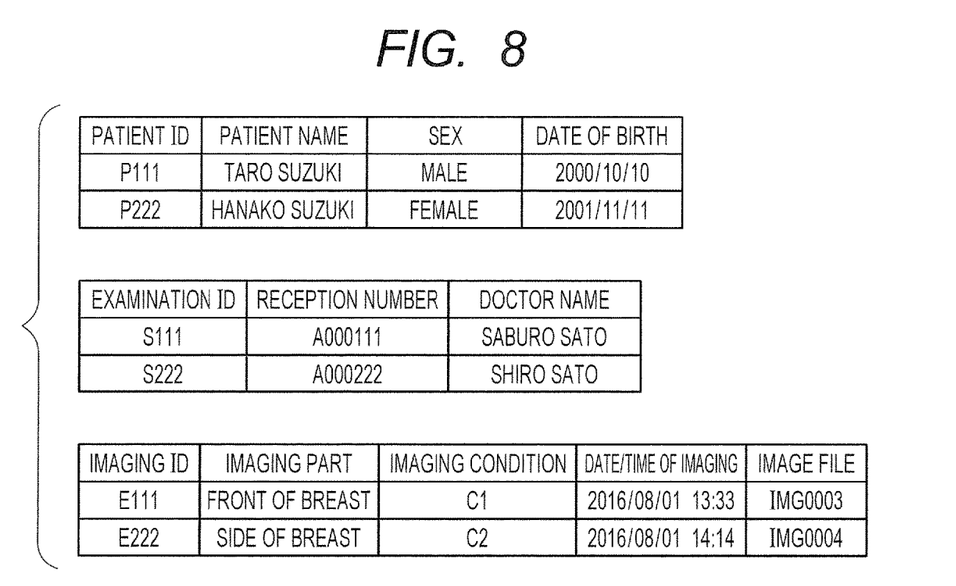
FIG. 8 is a diagram for illustrating an example of collation information held in a storage.

For example, as illustrated in FIG. 8, the collation information held in the storage 22 is a table for associating various types of information and identification information with each other. In the tables of FIG. 8, a patient ID and patient information are associated with each other, an examination ID, a reception number, and a doctor name are associated with one other, and an imaging ID, imaging information, and image data are associated with one other. When a patient ID is used as the identification information of the patient information, the radiation imaging apparatus 1 refers to a table of the storage 22 to identify the patient information, for example, a patient name. Further, also for the examination order, the imaging information, and the information, the radiation imaging apparatus 1 may similarly refer to the tables of the storage 22 based on the identification information to identify various types of information.

The storage 22 stores the radiation image output from the detection apparatus 7 and the examination information generated by the examination generation unit 23 (Step S307).

As described above, the radiation imaging apparatus transmits the related information to the detection apparatus, and the detection apparatus attaches the related information to the image data, and thus the radiation imaging apparatus associates the radiation image and the examination order with each other based on the attached related information, to thereby generate the examination information. As a result, the radiation imaging apparatus can control acquisition of a radiation image finely.

According to the embodiments described above, through acquisition of information (supplementary information) on a radiation image from the detection apparatus, the radiation imaging apparatus can control acquisition of the radiation image finely.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-219179, filed Nov. 9, 2016, which is hereby incorporated by reference herein in its entirety.

What is claimed is:

1. A radiation imaging apparatus, comprising:
   an information acquisition unit configured to acquire information on a radiation image from a detection apparatus configured to take the radiation image by detecting radiation;
   a transfer request unit configured to transmit to the detection apparatus, based on the information, a transfer request signal for requesting transfer of an untransferred radiation image taken by and stored in the detection apparatus; and
   an image acquisition unit configured to acquire the radiation image from the detection apparatus.

2. The radiation imaging apparatus according to claim 1, wherein the information acquisition unit is configured to acquire, as the information, information on at least one of an image ID, imaging date, imaging time, completion of transfer, incompletion of transfer, number of transferred radiation images, number of untransferred radiation images, transfer date, or transfer time of the radiation image.

3. The radiation imaging apparatus according to claim 1, wherein the information acquisition unit is configured to acquire a number of untransferred radiation images as the information, and to cause a display unit to display the information.

4. The radiation imaging apparatus according to claim 1, further comprising a connection detection unit configured to detect a communication connection to the detection apparatus,
   wherein the information acquisition unit is configured to acquire the information when the connection detection unit detects the communication connection to the detection apparatus.

5. The radiation imaging apparatus according to claim 1, further comprising:
   a connection detection unit configured to detect a communication connection to the detection apparatus; and
   a display unit configured to display the information,
   wherein the display unit is configured to display pieces of the information preferentially in an order in which the connection detection unit detects the communication connection to the detection apparatus.

6. The radiation imaging apparatus according to claim 1, further comprising a display unit configured to display the information,
   wherein the display unit is configured to display the information on an untransferred radiation image with priority over the information on a transferred radiation image.

7. The radiation imaging apparatus according to claim 1, further comprising a display unit configured to display the information,
   wherein the display unit is configured to display the information on an untransferred radiation image in a display mode different from a display mode of the information on a transferred radiation image, and
   wherein the transfer request unit is configured to transmit the transfer request signal to the detection apparatus when the display mode of the information on the untransferred radiation image is operated.

8. The radiation imaging apparatus according to claim 1, further comprising a designation unit configured to designate a transfer order of untransferred radiation images.

9. The radiation imaging apparatus according to claim 1, further comprising an examination generation unit configured to acquire from the detection apparatus at least one of subject-to-be-examined information on a subject to be examined of radiation imaging, imaging information on the radiation imaging, detection apparatus information on the detection apparatus, or information on the radiation image as supplementary information attached to the radiation image, and to generate examination information in which the radiation image and an examination order relating to an examination request for the radiation imaging are associated with each other based on, of the supplementary information, related information related to the examination order.

10. The radiation imaging apparatus according to claim 9, further comprising an input unit configured to input, based on the supplementary information, the related information for associating the radiation image and the examination order with each other,
    wherein the examination generation unit is configured to generate the examination information based on the input related information.

11. The radiation imaging apparatus according to claim 10, wherein, based on a section of at least one of the subject-to-be-examined information, the imaging information, the detection apparatus information, or the information, the supplementary information is attached to the radiation image for each section.

12. The radiation imaging apparatus according to claim 1, further comprising:
    an information transmission unit configured to transmit to the detection apparatus at least one of an examination order relating to an examination request for radiation imaging, subject-to-be-examined information on a subject to be examined of the radiation imaging, or imaging information on the radiation imaging as related information related to the examination order; and
    an examination generation unit configured to generate, based on the related information, examination information in which the radiation image and the examination order are associated with each other.

13. The radiation imaging apparatus according to claim 12, wherein the information acquisition unit is configured to cause a display unit to display a number of examinations corresponding to a number of untransferred radiation images as supplementary information attached to the radiation image.

14. A radiation imaging system, comprising:
    a radiation generation unit configured to generate radiation;
    a detection unit configured to take a radiation image by detecting the radiation;
    an information acquisition unit configured to acquire information on the radiation image from the detection unit;
    a transfer request unit configured to transmit to the detection unit, based on the information, a transfer request signal for requesting transfer of an untransferred radiation image taken by and stored in the detection unit; and
    an image acquisition unit configured to acquire the radiation image from the detection unit.

15. A radiation imaging method, comprising:
    acquiring information on a radiation image from a detection apparatus configured to take the radiation image by detecting radiation;
    transmitting to the detection apparatus, based on the information, a transfer request signal for requesting transfer of an untransferred radiation image taken by and stored in the detection apparatus; and
    acquiring the radiation image from the detection apparatus.

16. A non-transitory computer-readable medium having stored thereon a program to be executed by a processor to cause the processor to execute each step of the radiation imaging method of claim 15.

17. A radiation imaging apparatus, comprising:
- an information acquisition unit configured to acquire information on a radiation image from a detection apparatus configured to take the radiation image by detecting radiation;
- a transfer request unit configured to transmit to the detection apparatus, based on the information, a transfer request signal for requesting transfer of a radiation image untransferred and stored in the detection apparatus;
- an image acquisition unit configured to acquire the radiation image from the detection apparatus; and
- a designation unit configured to designate a transfer order of untransferred radiation images.

* * * * *